United States Patent
Fujii et al.

(10) Patent No.: US 7,764,373 B2
(45) Date of Patent: Jul. 27, 2010

(54) FINE PARTICLE CONSTITUENT MEASURING METHOD AND FINE-PARTICLE CONSTITUENT MEASURING APPARATUS

(75) Inventors: Takashi Fujii, Kanagawa (JP); Naohiko Goto, Tokyo (JP); Megumi Miki, Kanagawa (JP); Takuya Nayuki, Kanagawa (JP); Koshichi Nemoto, Kanagawa (JP); Nobuyuki Tanaka, Tokyo (JP)

(73) Assignee: Central Research Institute of Electric Power Industry, Tokyo (JP)

( * ) Notice: Subject to any disclaimer, the term of this patent is extended or adjusted under 35 U.S.C. 154(b) by 192 days.

(21) Appl. No.: 12/067,381

(22) PCT Filed: Sep. 20, 2006

(86) PCT No.: PCT/JP2006/318647
§ 371 (c)(1),
(2), (4) Date: Mar. 19, 2008

(87) PCT Pub. No.: WO2007/034840
PCT Pub. Date: Mar. 29, 2007

(65) Prior Publication Data
US 2009/0180114 A1    Jul. 16, 2009

(30) Foreign Application Priority Data
Sep. 20, 2005   (JP) .............................. 2005-272665

(51) Int. Cl.
*G01J 3/30* (2006.01)
(52) U.S. Cl. ..................................................... 356/318
(58) Field of Classification Search ................. 356/318, 356/316
See application file for complete search history.

(56) References Cited

U.S. PATENT DOCUMENTS

| 6,184,517 B1 | 2/2001 | Sawada et al. |
| 2002/0015150 A1 | 2/2002 | Armstrong et al. |
| 2008/0180655 A1* | 7/2008 | Bruch et al. .................. 356/73 |

FOREIGN PATENT DOCUMENTS

| EP | 1368624 A | 12/2003 |
| JP | 6-247398 A | 9/1994 |
| JP | 10-300671 A | 11/1998 |

(Continued)

OTHER PUBLICATIONS

Wakamatsu et al., "Particle Diameter and Composition Concurrent Measurement of Fine Particles by Plasma Atomic Emission Spectroscopy" J. Aerosol Res./vol. 19, pp. 28-33, 2004.

(Continued)

*Primary Examiner*—Tarifur Chowdhury
*Assistant Examiner*—Abdullahi Nur
(74) *Attorney, Agent, or Firm*—Notaro, Michalos & Zaccaria P.C.

(57) ABSTRACT

Fine particles such as nanoparticles and microparticles is irradiated to generate plasma by focusing an ultrashort pulse laser beam 15 emitted from a laser device 16. More preferably, the plasma is generated by a filament 14 generated in the ultrashort pulse laser beam 15. A constituent of the fine particles is measured based on an emission spectrum from the plasma.

14 Claims, 15 Drawing Sheets

FOREIGN PATENT DOCUMENTS

| | | |
|---|---|---|
| JP | 2002-5833 A | 1/2002 |
| JP | 2004-530867 A | 10/2004 |
| JP | 2005-9948 A | 1/2005 |
| WO | WO 02-071013 | 9/2002 |

OTHER PUBLICATIONS

C. Favre et al., "White-Light Nanosource with Directional Emission" Phys. Rev. Lett. pp. 035002-035005, 2002.

S. Borrmann et al., "Lasing on Cloudy Afternoon" Nature, vol. 418, pp. 826-827, 2002.

J. Kasparian et al., "White-Light Filaments for Atmospheric Analysis" Science, vol. 301, pp. 61-64, 2003.

G. Mejean et al., "Remote Detection and Identification of Biological Aerosols Using a Femtosecond Terawatt Lidar System", Appl. Phys. B, vol. B78, pp. 535-537, 2004.

* cited by examiner

11

11

11

FINE PARTICLE CONSTITUENT MEASURING METHOD AND FINE-PARTICLE CONSTITUENT MEASURING APPARATUS

TECHNICAL FIELD

The present invention relates to a method and apparatus for measuring a constituent of fine particles such as a nanoparticles and a microparticles. More particularly the invention relates to a fine-particle constituent measuring method and a fine-particle constituent measuring apparatus in which plasma is generated using an ultrashort pulse laser, and an emission spectrum from the plasma is measured, thereby measuring the constituent of the fine particles.

BACKGROUND ART

Conventionally, laser-induced breakdown spectroscopy (LIBS) with a nanosecond laser whose pulse width exists in a nanosecond (ns) range is used in in-situ constituent measurement of the nanoparticles or microparticles (Non-Patent Document 1). Recently, there is proposed a technique in which a target substance is irradiated with an ultrashort pulse laser to observe a spectrum of plasma generated by natural focusing in the substance, thereby measuring the constituent of particles having diameters of several micrometers or more (Non-Patent Documents 2 and 3). There is also reported a result of which a constituent of biological particles is remotely measured at a distance of 50 m by utilizing multi-photon absorption of the ultrashort pulse laser (Non-Patent Documents 4 and 5).

Non-Patent Document 1: Wakamatsu et al., "Particle Diameter and Composition Concurrent Measurement of Fine Particles by Plasma Atomic Emission Spectroscopy", J. Aerosol Res./Vol. 19, PP. 28-33, 2004.

Non-Patent Document 2: C. Favre et al., "White-Light Nanosource with Directional Emission", Phys. Rev. Lett., pp. 035002-035005, 2002.

Non-Patent Document 3: S. Borrmann et al., "Lasing on cloudy afternoon", Nature, Vol. 418, pp. 826-827, 2002

Non-Patent Document 4: J. Kasparian et al., "White-light filaments for atmospheric analysis", Science, Vol. 301, PP. 61-64, 2003.

Non-Patent Document 5: G. Mejean et al., "Remote detection and identification of biological aerosols using a femtosecond terawatt lidar system", Appl. Phys. B, Vol. B78, pp. 535-537, 2004.

DISCLOSURE OF THE INVENTION

Problem to be Solved by the Invention

However, in LIBS with the nanosecond laser, because a laser beam has a long pulse width, a plasma is generated in a crest portion of the laser pulse, and laser beam energy is not efficiently absorbed in the measuring target substance, which results in a problem of weak emission. Although the technique of irradiating the target substance with the ultrashort pulse laser beam to observe the spectrum of the plasma generated by the natural focusing in the substance is applicable to the particles having particle diameters of a micrometer (μm) or more, unfortunately the technique is hardly applicable to the particles having particle diameters of a nanometer (nm) or less because the beam is not naturally focused in the particles efficiently. In the method in which the multi-photon absorption is utilized, it is necessary to tune a laser wavelength to an absorption spectrum of an atom or a molecule, so that disadvantageously plural constituents are hardly measured at the same time.

An object of the present invention is to provide a fine-particle constituent measuring method and a fine-particle constituent measuring apparatus which can be applied to the fine particles having the particle diameters of the order of nanometers to simultaneously measure the plural constituents while causing the measuring target substance to efficiently absorb laser beam energy.

Means for Solving the Problem

In order to attain the above object, in a fine-particle constituent measuring method according to the present invention, an ultrashort pulse laser beam is focused to fine particles to generate plasma and a constituent of said fine particles is measured based on an emission spectrum from the plasma. The emission spectrum from the plasma varies depending on the substance, so that the constituent of the fine particles can be identified based on the emission spectrum.

Preferably the ultrashort pulse laser beam includes a filament generated by irradiation thereof. The filament is generated by the irradiation of the ultrashort pulse laser beam, and is irradiated to the fine particles to generate the plasma.

In the fine-particle constituent measuring method according to the invention, preferably generating the filament is conducted during a beam propagation process while a reflecting mirror having a local projection or recess is irradiated with the ultrashort pulse laser beam, and an intensity spot is formed at any position of a beam cross-section reflected from the local projection or recess and set to a starting point of the filament generation. In the ultrashort pulse laser beam with which the reflecting mirror having the local projection or recess is irradiated, local spatial modulation is imparted to the beam wavefront according to the local projection or recess of the mirror surface during the reflection, and the local spatial modulation becomes the starting point (seed) to form the filament in the beam propagation process. Because the filament is stably generated by the existence of the local projection or recess of the reflecting mirror surface, the local projection or recess is formed at any position to uniquely and continuously form the filament at any position in the beam cross-section.

In the fine-particle constituent measuring method according to the invention, preferably a recess which is global relative to the local projection or recess is provided around the local projection or recess of the reflecting mirror, and energy of the ultrashort pulse laser beam reflected by the global recess or the surrounding intensity spots are gathered around the intensity spot which becomes the starting point of the filament generation. In this case, the position where the intensity spot is formed by the local projection or recess is previously correlated with the position where the energy of the ultrashort pulse laser beam reflected by the global recess or the surrounding intensity spots are gathered, and an electric field intensity of the intensity spot is further strengthened more surely at any position in the beam cross-section.

In the fine-particle constituent measuring method according to the invention, preferably a reflecting mirror having a local projection or recess is irradiated with the ultrashort pulse laser beam, and an intensity spot is formed at any position of a beam cross-section reflected from the local projection or recess and set to a starting point of the filament generation, a reflecting mirror having a global recess is also irradiated with the ultrashort pulse laser beam, the global recess being global relative to the local projection or recess, the global recess being provided around the local projection or recess of the beam cross-section, and energy of the ultrashort pulse laser beam reflected by the global recess or the surrounding intensity spots are gathered around the intensity spot which becomes the starting point of the filament generation. In this case, the gathering of the energy of the ultrashort pulse laser beam reflected by the global recess or the surrounding intensity spots is controlled independently of the intensity spot uniquely formed at any position of the beam cross-section after the beam is reflected by the local projection or recess.

In the fine-particle constituent measuring method according to the invention, preferably the reflecting mirror is a deformable mirror whose reflection plane can arbitrarily be deformed. In this case, when the reflection plane shape of the reflecting mirror is changed, the position of the local projection or recess or global recess can be changed to control the position where the filament is generated.

In the fine-particle constituent measuring method according to the invention, preferably white-light spectral intensity is reduced by giving a temporal delay to measurement of the emission spectrum. In this case, the temporal delay is given to the measurement of the emission spectrum, so that the emission spectrum can be measured after the white light propagates.

In the fine-particle constituent measuring method according to the invention, preferably light emitted from the plasma is focused using a receiver telescope. In this case, the fine particles constituent can remotely be measured.

A fine-particle constituent measuring apparatus according to the invention includes a laser device which outputs an ultrashort pulse laser beam; a beam-focusing device which focuses the ultrashort pulse laser beam to irradiate fine particles; a light reception device which receives plasma generated from the fine particles by the focusing of the ultrashort pulse laser beam; and a spectrum analyzer which identifies a constituent of the fine particles based on an emission spectrum from the plasma. In the fine-particle constituent measuring apparatus according to the second aspect of the invention, preferably the beam-focusing device forms an intensity spot in the ultrashort pulse laser beam to generate a filament during a process of focusing the ultrashort pulse laser beam.

In the fine-particle constituent measuring apparatus according to the invention, preferably the beam-focusing device includes a reflecting mirror having a local projection or recess, and the reflecting mirror is irradiated with the ultrashort pulse laser beam, and an intensity spot is formed at any position of a beam cross-section reflected from the local projection or recess and set to a starting point of the filament generation.

In the fine-particle constituent measuring apparatus according to the invention, preferably a recess which is global relative to the local projection or recess is provided around the local projection or recess of the reflecting mirror of the beam-focusing device, and energy of the ultrashort pulse laser beam reflected by the global recess or the surrounding intensity spots are gathered around the intensity spot which becomes the starting point of the filament generation.

In the fine-particle constituent measuring apparatus according to the invention, preferably the beam-focusing device includes a first reflecting mirror and a second reflecting mirror which are disposed on a path for focusing the ultrashort pulse laser beam, the first reflecting mirror and second reflecting mirror continuously reflecting the ultrashort pulse laser beam, the first reflecting mirror has the local projection or recess in a reflection plane thereof, the second reflecting mirror has a reflection plane which forms a global recess at a position corresponding to a surrounding of the local projection or recess of the beam cross-section, the global recess being global relative to the local projection or recess of the first reflecting mirror, and the beam-focusing device forms an intensity spot in an arbitrary position of a cross section of the beam reflected by the first reflecting mirror, and the beam-focusing device gathers energy of the ultrashort pulse laser beam reflected by the second reflecting mirror or the surrounding intensity spots around the intensity spot which becomes the starting point of the filament generation.

In the fine-particle constituent measuring apparatus according to the invention, preferably the reflecting mirror is a deformable mirror whose reflection plane can arbitrarily be deformed.

In the fine-particle constituent measuring apparatus according to the invention, preferably the light reception device reduces white-light spectral intensity by giving a temporal delay to measurement of the emission spectrum.

In the fine-particle constituent measuring apparatus according to the invention, preferably the light reception device includes a receiver telescope which focuses light emitted from the plasma of the fine particles.

EFFECT OF THE INVENTION

According to the fine-particle constituent measuring method and apparatus of the present invention, the plasma is generated by focusing the ultrashort pulse laser beam onto the fine particles which is of the target substance, and the emission spectrum is observed from the plasma, thereby measuring the spectrum of the fine particles which is of the target substance. Therefore, the particles having the particle diameter of the nanometer region can be measured because the natural focusing in the particles is not utilized. The spectra of the plural substances are simultaneously measured, so that the constituents of the plural substances can simultaneously be measured. Because the ultrashort pulse laser of the femtosecond region is used, the irradiation of the laser pulse is ended before the plasma is grown. Therefore, the laser energy can efficiently be absorbed in the measuring target substance, and emission efficiency of the measuring target substance can be improved.

In the fine-particle constituent measuring method and apparatus of the invention, in the case of the use of the filament generated by the propagation of the ultrashort pulse laser beam through the air, liquid, and solid, the plasma emission is integrated in the laser beam traveling direction, so that the plasma emission intensity can significantly be improved.

Accordingly, in the in-situ measurement and remote measurement, the constituent of the fine particles can efficiently be measured by placing, e.g., an optical fiber or a receiver telescope at the back of the laser beam. The filament is the laser beam which propagates while being focused narrowly, and the longer filament can be generated by the use of the ultrashort pulse laser beam. Therefore, usually the plasma is produced in the filament to form a plasma channel. This enables the emission efficiency to be improved in the measuring target substance.

In the fine-particle constituent measuring method and apparatus of the invention, in the case of the use of the reflecting mirror having the local projection or recess as the technique of controlling the generation of the filament generated by the propagation of the ultrashort pulse laser beam, the filament can be generated at any position previously designed. Usually the filament is temporally and spatially generated in an accidental manner according to the intensity distribution in the laser beam, and the position and time of the filament generation are hardly controlled during the propagation of the laser beam. However, in the invention, the local spatial modulation is imparted to the beam wavefront during the reflection of the laser beam according to the local projection or recess of the mirror surface using the reflecting mirror having the local projection or recess, and the filament is formed in the beam propagation process while the local projection or recess is set to the starting point (seed). Therefore, the generation position and intensity of the filament can easily be controlled in real time, and the efficiency of the fine particles constituent measurement with the filament can be improved. Usually the filament is generated when the beam propagates through a certain distance. However, according to the invention, because the filament can be generated in the shorter propagation distance, particularly the effective in-situ measurement is performed.

In the fine-particle constituent measuring method and apparatus of the invention, the laser beam intensity can be concentrated on any position when the reflecting mirror in which the global recess global relative to the local projection or recess is added to the local projection or recess is used as the technique of generating and controlling the filament. Therefore, the energy of the ultrashort pulse laser beam reflected by the global recess or the surrounding intensity spots are gathered around the intensity spot which is formed at any position in the cross section of the beam reflected by the local projection or recess, so that the electric field intensity of the intensity spot can further be strengthened at any position to more surely generate the filament during the beam propagation. The same holds true for the case in which the local projection or recess and the global recess are realized in the reflection of the different reflecting mirrors.

In the fine-particle constituent measuring method and apparatus of the invention, when the deformable mirror is used as the reflecting mirror, the position where the filament is generated in the beam cross-section can be changed in real time by changing the shape of the reflection plane. Therefore, the filament can be generated at an optimum position even if the filament generation conditions are changed by a change in climate condition and the like.

In the fine-particle constituent measuring method and apparatus of the invention, when the temporal delay is given to the measurement of the emission spectrum, the emission spectrum can be measured after the white light propagates. Therefore, the intensity of the white-light spectrum which is of a noise (N) can be decreased to improve an S/N ratio of the spectrum of the measuring target substance which is of an objective signal (S).

In the fine-particle constituent measuring method and apparatus of the invention, the remote measurement can be performed when the emission is focused with the receiver telescope.

BRIEF DESCRIPTION OF THE DRAWINGS

FIG. 1 is a schematic diagram showing a state in which a trace aerosol constituent in air is remotely measured.

FIG. 5(A) shows a wavefront of an incident beam, and FIGS. 5(B) to 5(D) show a change over time in wavefront of the beam reflected by a reflection plane having the local projection.

FIG. 15 is a schematic diagram showing a state in which a cloud constituent is remotely measured.

FIG. 16 is a schematic diagram showing a state in which fine particles in air is measured in-situ.

FIG. 23(b) is a view showing the emission spectrum of the alcohol lamp in which the salt is dissolved.

EXPLANATIONS OF LETTERS OR NUMERALS 2 deformable mirror (reflecting mirror)
9 local projection
10 global recess
14 filament
15 ultrashort pulse laser beam
19 receiver telescope

BEST MODE FOR CARRYING OUT THE INVENTION

A configuration of the present invention will be described in detail with reference to best modes shown in drawings.

Figure 1:
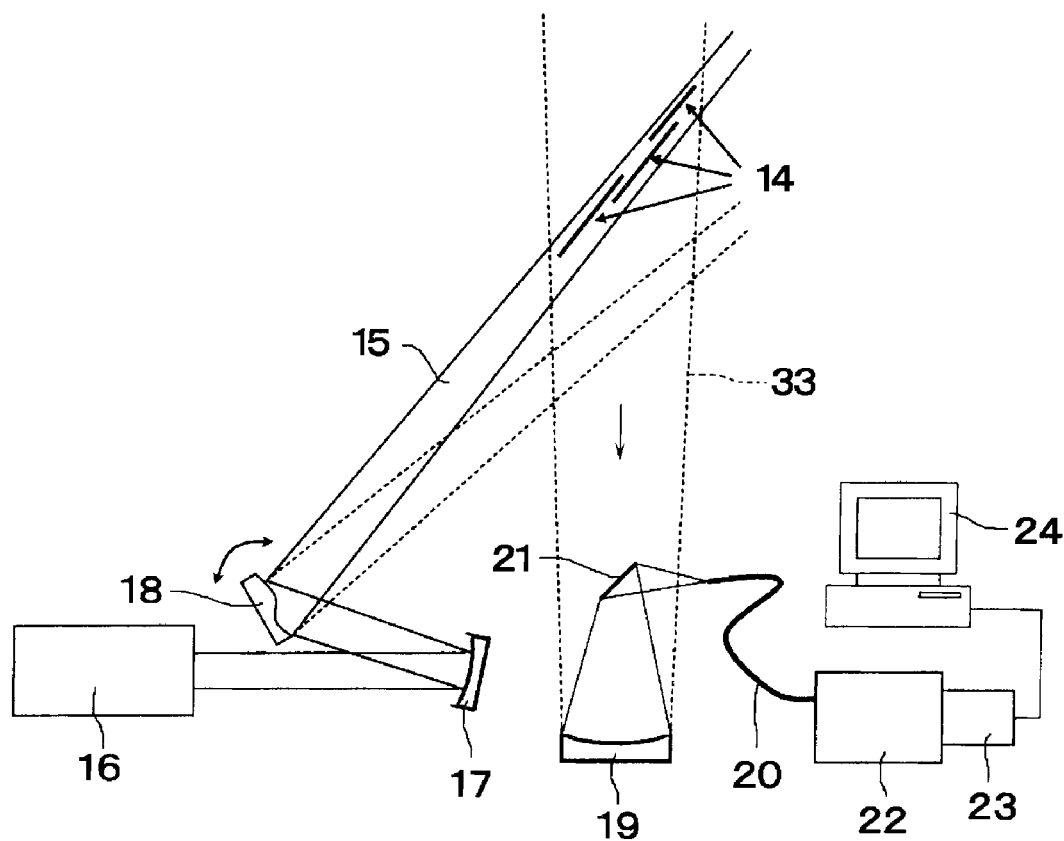
FIG. 1 shows a first embodiment of the present invention.

FIG. 1 shows a first embodiment in which the invention is applied to a fine-particle constituent measuring method and apparatus for remotely measuring a trace aerosol constituent in air using a lidar. In the fine-particle constituent measuring apparatus, filaments 14 are generated by irradiating air with an ultrashort pulse laser beam 15 outputted from a laser device 16, fine particles such as nanoparticles or microparticles which are of a measuring target are irradiated with filaments 14 to generate the plasma, and constituents of the fine particles are measured based on an emission spectrum from the plasma. A beam-focusing device includes a concave mirror 17 and a surface shape deformable mirror 18 for focusing the ultrashort pulse laser beam 15 to irradiate the fine particles. A light reception device receives light of the plasma from the fine particles generated by the focusing of the ultrashort pulse laser beam 15, and the light reception device includes a receiver telescope 19, an secondary mirror 21, a bundle fiber 20, a spectrometer 22, and an ICCD (Intensified CCD) camera 23. A spectrum analyzer identifies the constituent of the fine particles based on the emission spectrum from the plasma, and the spectrum analyzer includes a computer 24. In the spectrum analyzer, pieces of information on intrinsic spectra possessed by various substances including the fine particles which is the measuring target are previously listed on a database and stored in storage means, and the substance is identified by a comparison of the spectrum measured by the light reception device and known spectral data.

Examples of the fine particles of the measuring target include nanoparticles having particle diameters of the order of nanometers, microparticles having particle diameters of the order of micrometers, particles having particle diameters of a nanometer or less, and particles having particle diameters of a micrometer or more. The ultrashort pulse laser beam 15 is a laser beam whose pulse width exists in a region of a picosecond (ps) or less. For example, the ultrashort pulse laser beam 15 can be emitted using a titanium-sapphire laser device, a glass laser device, or a fiber laser device.

The ultrashort pulse laser beam 15 emitted from the laser device 16 is reflected by the concave mirror 17 and the surface shape deformable mirror 18, and the air is irradiated with the ultrashort pulse laser beam 15. The ultrashort pulse laser beam 15 generates the filament 14 while being gently focused. An aerosol in the air irradiated with the filament 14 becomes the plasma, the light emissions from the filament 14 including the light emission of the plasma are focused by a receiver telescope 19 which is placed in noncoaxial with the ultrashort pulse laser beam 15, and the light emissions are incident to a bundle fiber 20. In the first embodiment, the light reflected from the receiver telescope 19 is reflected by an secondary mirror 21 and incident to the bundle fiber 20.

The light outgoing from the bundle fiber 20 is incident to a spectrometer 22, the light is received by an ICCD camera 23 after spectral dispersion is performed, and the aerosol constituent in the air is identified based on the spectrum. That is, the emission spectrum from the observed plasma is matched with the intrinsic spectrum possessed by each substance, which allows aerosol constituent in the air to be identified. The spectral matching is performed using the personal computer 24 in which the pieces of information on the intrinsic spectra possessed by the substances are stored.

In the first embodiment, the receiver telescope 19 is placed in noncoaxial with the laser beam, and gate timing of the ICCD camera 23 is adjusted to reduce an influence of the white light generated from the filament 14 on the measurement of the emission spectrum. That is, when the ultrashort pulse laser beam 15 is placed in coaxial with the receiver telescope 19, even if the gate timing of the ICCD camera 23 is delayed and set after the white light propagates, the ICCD camera 23 receives the backscattered light after the once-generated white light propagates, so that the influence of the white light is hardly eliminated. On the other hand, as shown in FIG. 1, when the ultrashort pulse laser beam 15 is noncoaxial with the receiver telescope 19, because the once-generated white light diverges from a visual field 33 of the receiver telescope 19 with the progress of the propagation, the gate timing of the ICCD camera 23 is set after the white light propagates (temporal delay), which allows the emission spectrum of the aerosol in the air to be observed with eliminating influence of the white light. Thus, the giving of the temporal delay to the measurement of the emission spectrum of the measuring target substance can decrease the white-light spectral intensity, so that an S/N ratio of the spectrum of the measuring target substance is improved.

As shown in FIG. 1, a propagation direction of the ultrashort pulse laser beam 15 can be changed by changing an angle of the surface shape deformable mirror 18. Therefore, because a distance between the receiver telescope 19 and the filament 14 entering the visual field 33 of the receiver telescope 19 can be changed, so that a measuring distance of the target substance can be changed. The first embodiment of FIG. 1 can also be applied to the remote measurement of asbestos or biological agents in air.

In the first embodiment, a position where the filament 14 is generated is controlled by adjusting a focal distance of the concave mirror 17 and a reflection plane shape of the surface shape deformable mirror 18. The control performed by the focal distance of the concave mirror 17 is supplementarily used, and the position where the filament 14 is generated is coarsely determined by the focal distance of the concave mirror 17. Then, the position where the filament 14 is generated is finely adjusted by changing the reflection plane shape of the surface shape deformable mirror 18. In other words, the concave mirror 17 is used in the coarse adjustment of the position where the filament 14 is generated, and the surface shape deformable mirror 18 is used in the fine adjustment. For example, in the in-situ measurement, the concave mirror 17 having the short focal distance is used to generate the filament 14 in the extremely-short propagation distance. On the contrary, in the lidar measurement, the generation of the filament 14 may be started after the ultrashort pulse laser beam 15 propagates through a relatively long distance. Instead, when the long filament 14 is desired to be generated, the concave mirror 17 having the long focal distance is used, or the concave mirror 17 is not used but only the surface shape deformable mirror 18 is used. Usually a plane mirror is used as the surface shape deformable mirror 18, and the surface shape deformable mirror 18 controls a phase distribution on a laser beam cross-section. Although the focal distance of the surface shape deformable mirror 18 is slightly changed by changing the reflection plane shape of the surface shape deformable mirror 18, preferably the concave mirror 17 is concurrently used to largely change the position where the filament 14 is generated in the case of the coarse adjustment. The surface shape deformable mirror 18 may be omitted, when the position where the filament 14 is generated can finely be adjusted by changing the reflection plane shape of the concave mirror 17 which is of the deformable mirror. However, practically the concave mirror 17 and the surface shape deformable mirror 18 are concurrently used because the fine control is hardly performed to the change in reflection plane shape of the concave mirror 17.

In the first embodiment, the propagation direction of the ultrashort pulse laser beam 15 is changed by changing the angle of the surface shape deformable mirror 18. Alternatively, the laser beam reflected from the surface shape deformable mirror 18 is reflected by a total reflection mirror (not shown in FIG. 1) to irradiate the air, and the propagation direction of the ultrashort pulse laser beam 15 may be changed by changing the angle of the total reflection mirror. In the case, the angle of the total reflection mirror is easily changed because the normal total reflection mirror has a simple structure compared with the surface shape deformable mirror. Therefore, advantageously the propagation direction of the ultrashort pulse laser beam is easily controlled.

Figure 2:
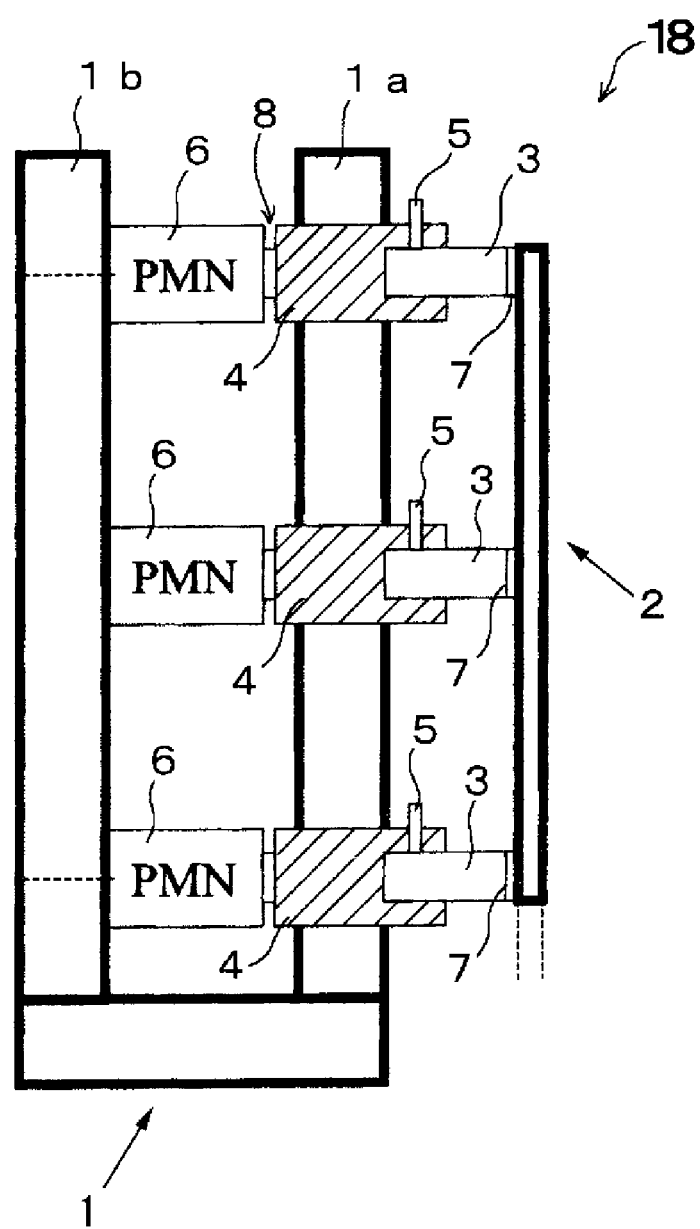
FIG. 2 is a schematic explanatory diagram showing an example of a surface shape deformable mirror.
Figure 3:
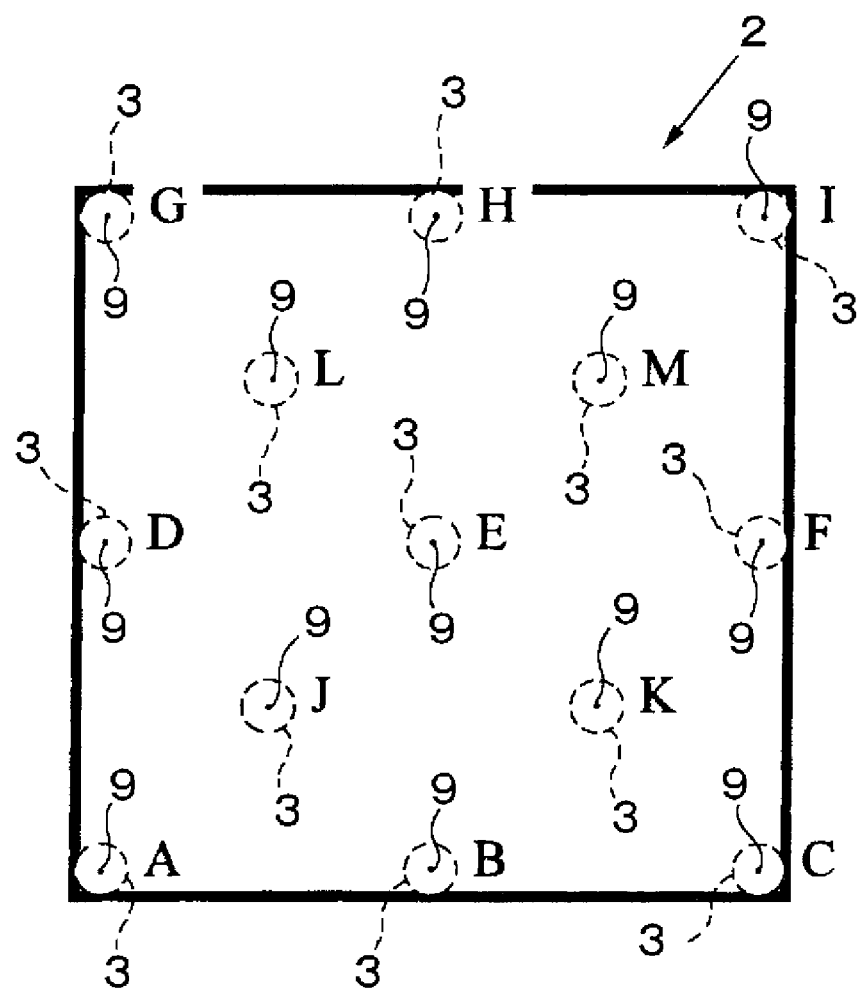
FIG. 3 is a front view (reflection plane side) showing a deformable mirror of the surface shape deformable mirror in FIG. 2.

The change in reflection plane shape of the surface shape deformable mirror 18 and the generation of the filament 14 will specifically be described below. FIGS. 2 and 3 show the surface shape deformable mirror 18. A deformable mirror including plural actuators which can independently be controlled is used in the surface shape deformable mirror 18. The surface shape deformable mirror 18 includes a reflecting mirror 2 (hereinafter referred to as a deformable mirror) whose reflection plane can arbitrarily be deformed and actuators 8 coupled to the backside of the deformable mirror 2 to impart displacement to the deformable mirror 2. In the surface shape deformable mirror 18, the deformable mirror 2 can globally be deformed by driving the actuator 8.

At this point, a thin plane mirror is adopted as the deformable mirror 2. In the thin plane mirror, the reflection plane can arbitrarily be deformed by driving the plural actuators 8 which can independently be controlled. In the first embodiment, the thin plane mirror has rigidity to an extent that a desired global recess can easily be formed by driving the actuators 8. For example, preferably the thin plane mirror having the thickness of about 3 mm is used in a square mirror having a length-and-width size of about 100×100 (mm).

The backside of the reflecting mirror 2 is coupled to the actuators 8, and the reflecting mirror 2 is supported by a frame 1 while the actuators 8 are interposed. In the first embodiment, thirteen actuators 8 are arranged in matrix and diagonal manners at substantially equal intervals over the backside of the deformable mirror 2. The number of actuators 8 is not limited to thirteen.

The actuator 8 includes a rod 3 bonded rigidly to the backside of the deformable mirror 2, and the rod 3 is coupled to a movable portion (in the first embodiment, rod holder 4) of the actuator 8 while being able to be separated from the rod holder 4. For example, a hole in which the rod 3 is fitted is made on at least an end portion side, to which the rod 3 is fixed, of the rod holder 4 fixed to an front end of a driving element 6, and the rod 3 is tightened by a screw 5 while a rear end side of the rod 3 is fitted in the hole, thereby detachably fixing the actuator 8. In the first embodiment, an outer peripheral surface of the rod 3 is pressed by the front end of the screw 5 secured in a screw hole of the rod holder 4, whereby the rod 3 is fixed by a friction force. In some cases, the rod 3 may detachably be coupled using a pin. When the rod 3 is formed in an easily detachable structure, the screw 5 is loosened to detach the rod 3 from the rod holder 4, and only the deteriorated deformable mirror 2 (including the rod 3 bonded to the backside thereof) can be replaced in the case where the replacement of the deformable mirror 2 is required due to the deterioration of reflection characteristics of the deformable mirror 2. That is, economically the rod holder 4, the actuator 8, and the support frame 1 can directly be reused.

In the first embodiment, as to the coupling between the actuator 8 and the deformable mirror 2, the front end of the rod 3 and the backside of the deformable mirror 2 are bonded to each other with an epoxy resin bonding agent 7. In the thin deformable mirror 2 having the thickness of 3 mm, an influence of a change in stress during curing of the bonding agent 7 is easily exerted on the mirror surface, and the surface side (reflection plane side) of the deformable mirror is slightly raised at a portion where the actuator 8 is bonded. For example, in the first embodiment, a projection 9 having a height of 0.4 μm is formed in the case where the rod 3 is bonded using the epoxy resin bonding agent 7. When the local projection or recess is formed by the curing or solidification of the bonding agent, spatial modulation which is locally imparted to the wavefront of the beam generated by the reflection of the ultrashort pulse laser beam sufficiently becomes a starting point forming the filament. The bump or dimple having the height of about 0.4 μm formed using the utilization of the bonding agent 7 can be formed in a manner that a mask with a hole is previously set, during producing the mirror surface of the deformable mirror 2 by evaporation, in front of a surface to be evaporated and the thickness of the mirror surface is locally controlled during the evaporation, allowing the formation of the local projection or recess.

Figure 7:
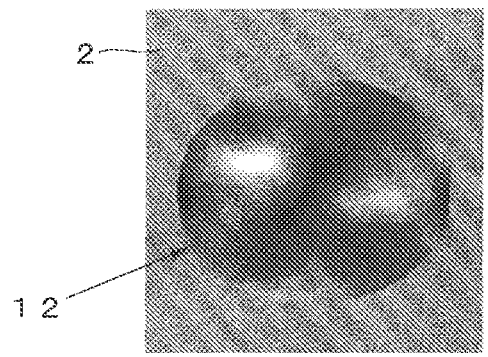
FIG. 7 is an explanatory view showing a surface shape of a deformable mirror having a thickness of 6 mm.
Figure 8:
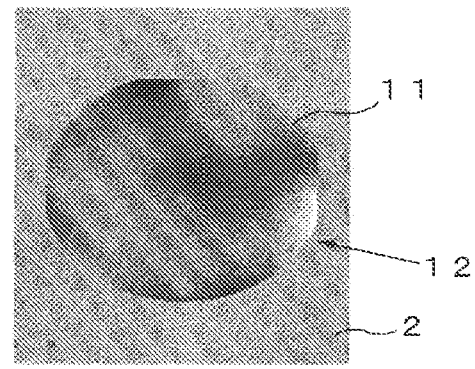
FIG. 8 is an explanatory view showing a surface shape of a deformable mirror having a thickness of 3 mm.
Figure 9:
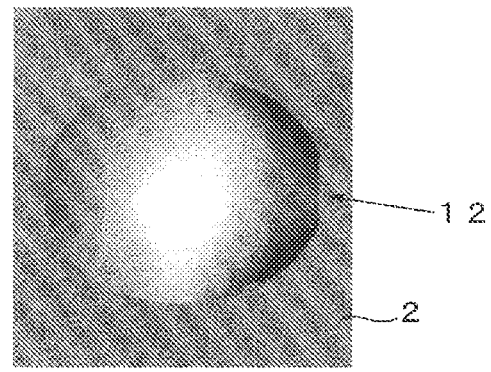
FIG. 9 is an explanatory view showing a surface shape when the deformable mirror of the embodiment is pushed out toward a mirror surface side to deform the deformable mirror in a raised manner with an actuator.

Sometimes the local projection 9 or recess is not formed by directly bonding the rod 3 with the bonding agent 7, even if the deformable mirror 2 has the thickness having flexibility to an extent at which the global recess can be formed. For example, FIG. 8 shows a surface shape of the deformable mirror 2 having the thickness of 3 mm. In the case, the point-like local bump (projection) or dimple (recess) is generated. On the other hand, FIG. 7 shows a surface shape of the deformable mirror 2 having the thickness of 6 mm. In the case, unlike the mirror of FIG. 8, the point-like local bump (projection) or dimple (recess) is not generated. This is attributed to the fact that the local bump or dimple is not formed by the compression or stress during the curing or solidification of the bonding agent because the deformable mirror is too thick. Therefore, preferably the mirror having the thickness of about 2 to 3 mm is used when the local projection or recess is formed in the mirror surface by the bonding of the rod 3. Unless the local projection or recess is formed by the direct bonding between the backside of the deformable mirror 2 and the actuator 8 using the bonding agent 7, for example when the local projection or recess is formed by the control of the evaporation film, the mirror having the thickness having the flexibility to an extent that a global recess 10 is formed by driving the actuator 8 can be used.

A driving source such as a piezoelectric element (PZT: Pb—Zr—Ti) or an electrostrictive element (PMN: Pb—Mg—Nb) which enables minute displacement of the deformable mirror is used as the driving element 6. Preferably the driving element such as the electrostrictive element is used because displacement direction and a displacement amount of the driving element can easily be controlled by changing magnitude or direction of an application voltage. However, the invention is not limited to the driving element such as the electrostrictive element. The driving element 6 is fixed to a wall 1b provided perpendicular to a base of the frame 1, and the rod holder 4 which becomes the movable portion is supported being able to advance and retreat in a back and forth directions (horizontal direction of FIG. 2) through a wall 1a having throughholes. The deformable mirror 2 is deformed so as to form the global recess 10 in a desired region of the deformable mirror 2 by appropriately controlling the drive of plural actuators 8 arranged in parallel to one another, i.e., by the combination of the actuator 8 pushing out the rod 3 and the actuator 8 pulling back the rod 3 or the combination of the actuator 8 pushing out the rod 3 and the actuator 8 not driven.

That the filament is generated by causing the ultrashort pulse laser beam 15, reflected from the surface shape deformable mirror 18, to propagate through the air will be described below. For the purpose of the simple explanation, the diameter of the ultrashort pulse laser beam 15 is set to $50\sqrt{2}$ mm with respect to the mirror having a side of 100 mm to take note of the five actuators (letters E, J, K, L, and M) near the center in the thirteen actuators.

Figure 5:
FIG. 5 is an explanatory view showing a change in wavefront before and after reflection of an ultrashort pulse laser beam.
Figure 5:
Figure 5:
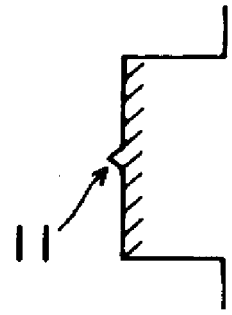
Figure 5:
Figure 5:
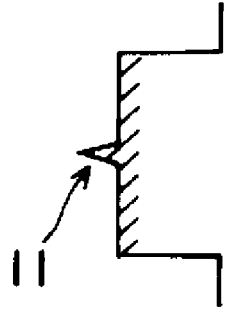
Figure 5:
Figure 5:
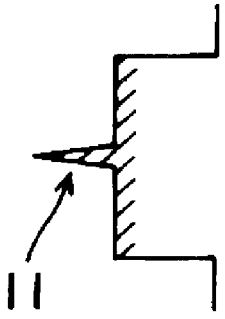
Figure 11:
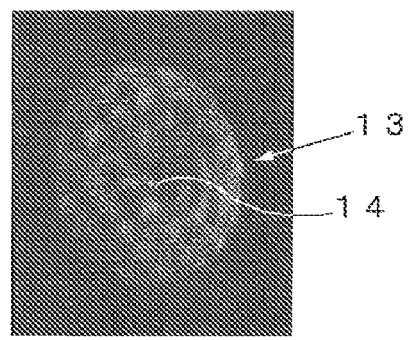
FIG. 11 is an explanatory view showing short-distance beam cross-section intensity.
Figure 12:
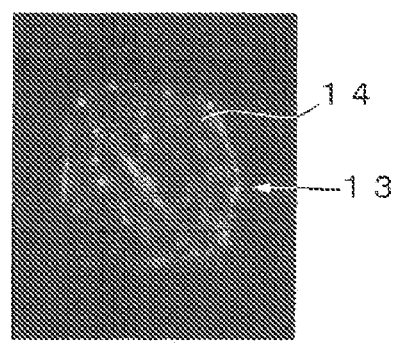
FIG. 12 is an explanatory view showing long-distance beam cross-section intensity.

First a method of forming the filament with only a reflecting mirror which has the local projection or recess in the reflection plane will be described. When the deformable mirror 2 in which the point-like local bump (projection) or dimple (recess) is generated as shown in FIG. 8 is placed on an optical path of the ultrashort pulse laser beam 15, even in the ultrashort pulse laser beam 15 having the shaped wavefront (see FIG. 5(A)), the local spatial modulation is imparted to the beam wavefront in the reflected beam according to the local projection or recess of the mirror surface (see FIG. 5(B)), the local spatial modulation imparted to the wavefront of the reflected beam 13 becomes more prominent during the propagation process of the reflected beam 13 (see FIGS. 5(C) and 5(D)), and the local spatial modulation becomes the starting point (seed) to generate the filament 14 in the beam propagation process. Because the filament 14 is stably generated by the existence of the local projection or recess in the surface of the reflecting mirror, the filament 14 is formed uniquely and continuously formed at any position of the beam cross-section by forming the local projection or recess at any position in the surface of the reflecting mirror. FIG. 11 shows a cross-section intensity distribution of the reflected beam 13 on a short range, and FIG. 12 shows a cross-section intensity distribution of the reflected beam 13 in a long range. Thus, it turns out that the single filament 14 is preferentially generated by the local projection 9 or recess formed in the mirror center portion. In the case where the ultrashort pulse laser beam 15 is reflected and propagated through the air, it is found that a starting point 11 of the filament 14 is generated by an intensity spot in a cross section of the reflected beam 13 and the filament 14 is grown in the progress of the propagation.

Figure 4:
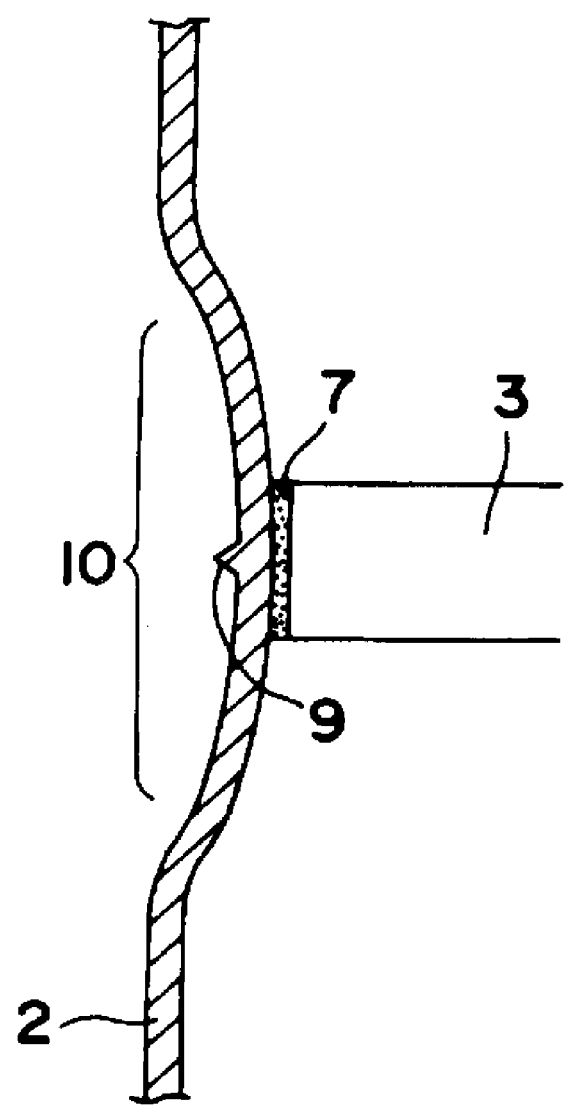
FIG. 4 is a principle view showing a relationship between a local projection and a global recess in a reflection plane of a mirror.
Figure 10:
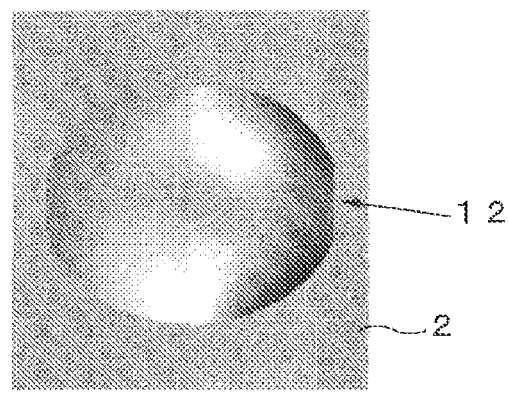
FIG. 10 is an explanatory view showing a surface shape when the deformable mirror of the embodiment is pulled toward a mirror backside to deform the deformable mirror in a recessed manner with the actuator.
Figure 13:
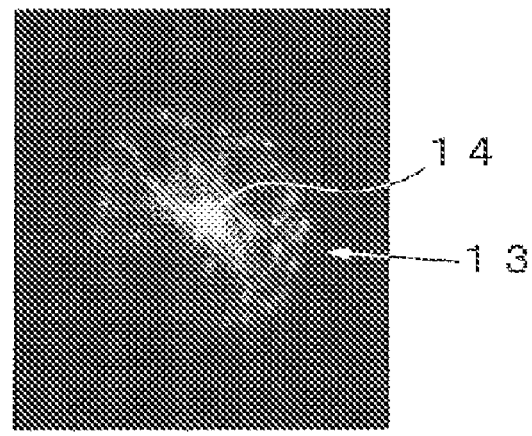
FIG. 13 is an explanatory view showing beam cross-section intensity when a mirror center portion of the deformable mirror of the embodiment is pulled to deform the deformable mirror in the recessed manner with the actuator.

Then, a method of forming the filament with a reflecting mirror which has the local projection 9 or recess and the global recess 10 larger than the local recess will be described. As shown in FIG. 10, the five actuators 8 designated by the letters E, J, K, L, and M are driven to pull the deformable mirror 2 from the backside, thereby globally sinking the surface side of the deformable mirror 2. Even in this state, the mirror surface shape is formed in the global recess 10 by the actuator as shown in FIG. 4, and the special surface shape in which the local projection 9 (or recess) exists is realized (see FIG. 11). Therefore, around the local projection 9 or recess or the position corresponding to surroundings of the local projection 9 or recess in the beam cross section, the energy of the reflected beam 13 or the surrounding intensity spots are gathered around the central intensity spot, and the electric field intensity of the intensity spot which becomes the starting point of the filament generation is further strengthened to generate more surely the filament in the beam propagation. FIG. 13 shows a state of the beam cross section when the center portion of the deformable mirror 2 is pulled. In the case where the actuator (E) of the mirror center portion corresponding to the beam center portion is pulled to form the global recess in the mirror center portion, the high-density filament 14 is formed while the surrounding intensity spots are gathered onto the beam center (see FIG. 13).

Figure 14:
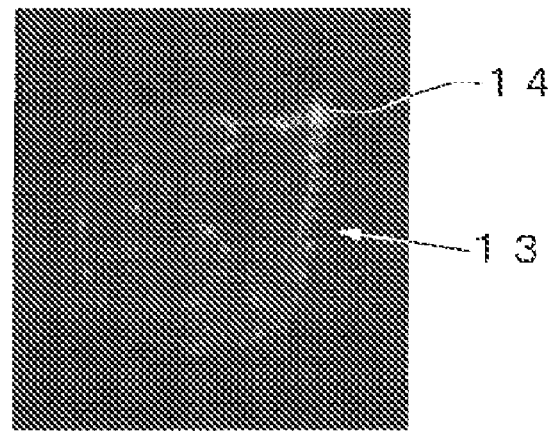
FIG. 14 is an explanatory view showing beam cross-section intensity when a mirror peripheral portion of the deformable mirror of the embodiment is pulled to deform the deformable mirror in the recessed manner with the actuator.

The position where the filament 14 is generated can be controlled by the control of the global recess forming position on the beam cross-section. For example, in the case where the actuator (E) of the mirror center portion corresponding to the beam center portion is pulled to form the global recess 10 in the mirror center portion, the high-density filament 14 is formed while the surrounding intensity spots are gathered onto the beam center (see FIG. 13). On the other hand, in the case where the actuator (M) of the reflecting mirror corresponding to the mirror peripheral portion (beam peripheral portion) in the region 12 irradiated with the beam is pulled to form the global recess in the mirror peripheral portion, the intensity spot also leans onto the beam peripheral portion, and the high-density filament 14 is formed while the formation of the filament becomes prominent in the peripheral portion (see FIG. 14). Therefore, it turns out that the position where the filament is prominently formed, i.e., the position where the high-density filament is formed can be controlled by the control of the position where the global recess is formed in the surface of the reflecting mirror even if the position of the local projection or recess which becomes the starting point of the filament generation is not change in the surface of the reflecting mirror.

Because the ultrashort pulse laser emitting apparatus can control the generation of the filament, for example, the generated filament can be applied to the control of an electric discharge path. In the case where the ultrashort pulse laser beam is propagated through the high-density gas, the generation of the plasma becomes more prominent compared with the case wherein the ultrashort pulse laser beam is propagated through the air. Because the laser electric field having the ultrahigh intensity is localized in the filament, electrons can be accelerated by interaction between the generated plasma and the laser electric field. In the case where the generated plasma is used as a light amplifying medium, dielectric emission is enabled to improve amplification efficiency using the long, continuous filament. In the case where the ultrashort pulse high-intensity laser is propagated through a sold-state medium such as glass, the filament is prominently generated. Because a composition of the medium is changed during the propagation, fine machining or modification can be performed by locally changing a refractive index or a transmittance, and an optical waveguide and the like can easily be formed using the long, continuous filament. Therefore, in addition to the techniques of laser triggered lightning, the invention can be applied to the atmospheric environment measurement of multi and concurrent measurement, the light amplification by induced emission with the filament as the light amplification medium, particle acceleration for electron acceleration, and laser processing for changing the composition of the medium.

Figure 15:
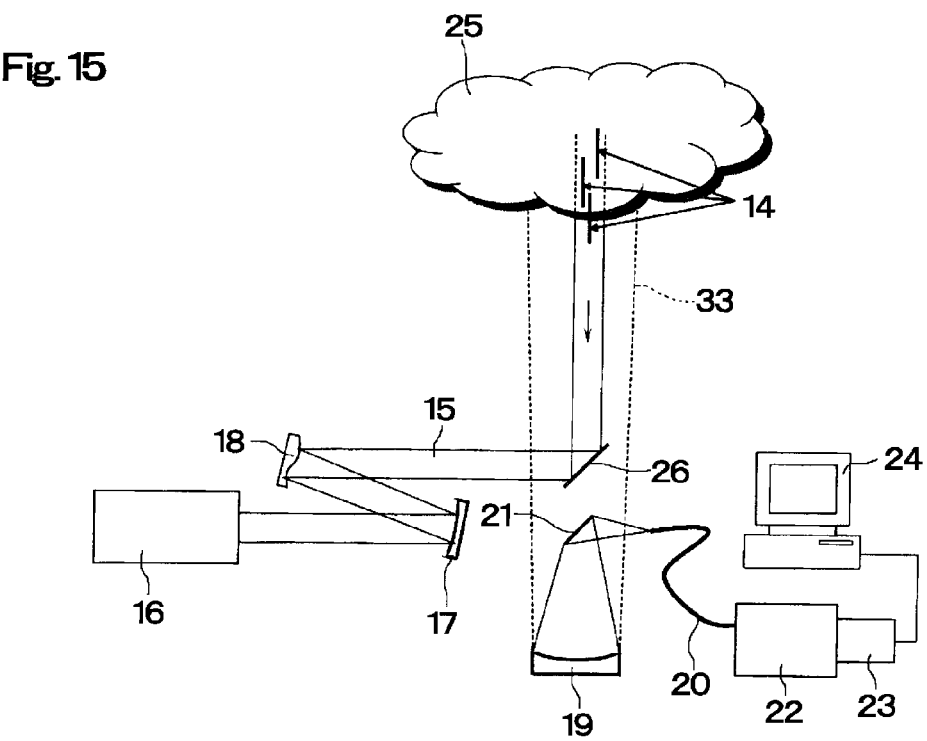
FIG. 15 shows a second embodiment of the invention.

A second embodiment in which the present invention is applied to fine-particle constituent measuring method and apparatus for remotely measuring a constituent of a cloud 25 will be described below with reference to FIG. 15. The same component as the fine-particle constituent measuring apparatus of FIG. 1 is designated by the same numeral, and the detailed description is omitted.

The fine-particle constituent measuring apparatus of the second embodiment is used to remotely measure the constituent of the cloud 25. The fine-particle constituent measuring apparatus of the second embodiment shown in FIG. 15 differs from the fine-particle constituent measuring apparatus of the first embodiment shown in FIG. 1 in that the optical axis of the ultrashort pulse laser beam 15 is coaxial with the optical axis of the receiver telescope 19 in the second embodiment shown in FIG. 15 while the optical axis of the ultrashort pulse laser beam 15 is noncoaxial with the optical axis of the receiver telescope 19 in the first embodiment shown in FIG. 1. In order that the optical axis of the ultrashort pulse laser beam 15 is set to be coaxial with the optical axis of the receiver telescope 19, the light reflected from the surface shape deformable mirror 18 is reflected by a total reflection mirror 26 placed on the backside of the secondary mirror 21 of the receiver telescope 19, and the air is irradiated with the ultrashort pulse laser beam 15. Because the cloud 25 has large particle density, the ultrashort pulse laser beam 15 and the white light generated by the filament 14 are hardly propagated. Therefore, as shown in FIG. 15, even if the optical axis of the ultrashort pulse laser beam 15 is coaxial with the optical axis of the receiver telescope 19, the backscattering of the ultrashort pulse laser beam 15 or white light has a little influence after the propagation from the measuring region. The lidar measurement can also be performed to the constituent of the cloud 25 even if the optical axis of the ultrashort pulse laser beam 15 is noncoaxial with the optical axis of the receiver telescope 19 as shown in FIG. 1.

A third embodiment in which the invention is applied to fine-particle constituent measuring method and apparatus enabling in-situ measurement for fine particles in air will be described below with reference to FIG. 16. The same component as the fine-particle constituent measuring apparatus of FIG. 1 is designated by the same numeral, and the detailed description is omitted.

The third embodiment differs from the first and second embodiments in that the receiver telescope 19 is not used because the lidar measurement is not performed. The fine particles in the air is sucked into a fine particle-filling cell 27. After the ultrashort pulse laser beam 15 is reflected by the concave mirror 17, the surface shape deformable mirror 18, and a dichroic mirror 28, the ultrashort pulse laser beam 15 is incident to the fine particle-filling cell 27 through a window 29. The ultrashort pulse laser beam 15 is reflected by the concave mirror 17 and the surface shape deformable mirror 18, thereby focusing the ultrashort pulse laser beam 15. The generation position and intensity of the filament 14 in the particle-filling cell 27 can be controlled by changing the reflection plane shape of the surface shape deformable mirror 18 in the above-described way. A beam damper 30 placed in the particle-filling cell 27 is irradiated with the ultrashort pulse laser beam 15 passing through the fine particle-filling cell 27.

The light emitted from the filament 14 and the scattered light of the white light generated by the ultrashort pulse laser beam 15 and filament 14 are transmitted through the window 29 and reach the dichroic mirror 28. At this point, the dichroic mirror 28 has characteristics in which the ultrashort pulse laser beam 15 is reflected while the light corresponding to the emission wavelength of the measuring substance is transmitted. Therefore, the scattering of the strong laser beam from the beam damper 30 is prevented from being incident to the bundle fiber 20. The light emitted from the filament 14 and the white light are incident to the spectrometer 22 through the bundle fiber 20, and the ICCD camera 23 receives the light to obtain the emission spectrum after the dispersion is performed to the light emitted from the filament 14 and the white light. The constituent of the fine particles in the air which is of the measuring target substance is identified by matching the emission spectrum with the intrinsic spectrum possessed by each substance. The gate timing of the ICCD camera 23 is changed to give the temporal delay, whereby the influence of the white light generated from the filament 14 on the emission spectrum measurement can be decreased.

Figure 16:
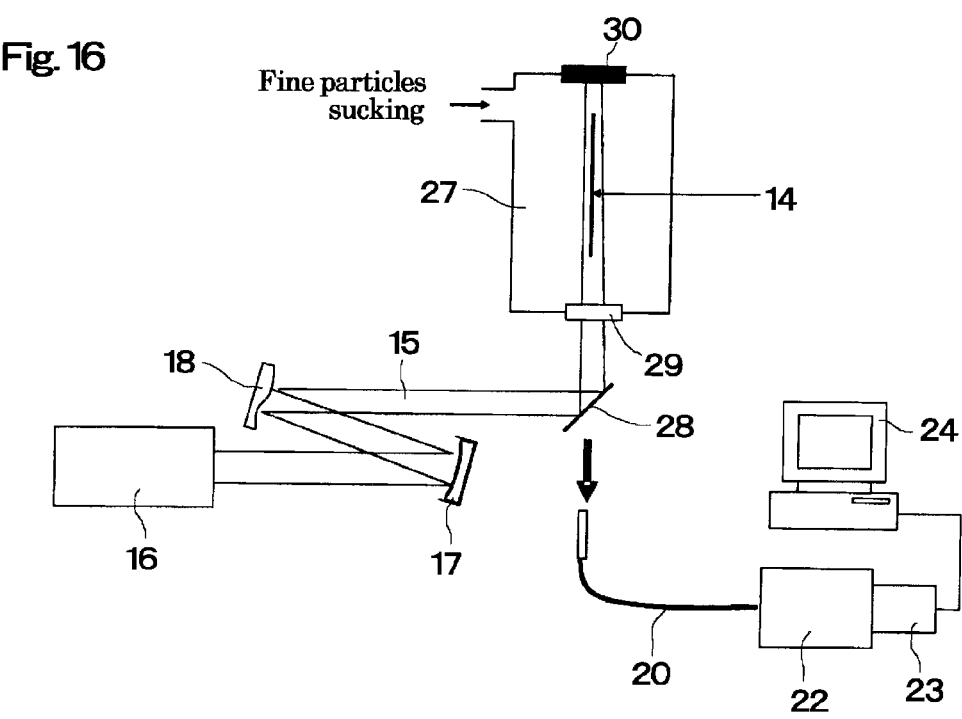
FIG. 16 shows a third embodiment of the invention.

In FIG. 16, the bundle fiber 20 is placed at the back of the dichroic mirror 28. Alternatively, another window is placed in the side face of the fine particle-filling cell 27, and the bundle fiber is placed while a filter transmitting only the light corresponding to the emission wavelength of the measuring substance is interposed, which allows the emission from the filament to be measured. In this case, although the emission integration effect is decreased in the filament because the emission of the filament is measured from a crosswise direction, the influence of the scattering of the strong laser beam from the beam damper 30 can be decreased.

The above embodiments are illustrated by way of example. However, the invention is not limited to the embodiments, but various modifications can be made without departing from the scope of the invention.

Although the ICCD camera 23 is used as the light reception element in the embodiments, the light reception element is not limited to the ICCD camera 23. For example, an array type semiconductor element may be used instead of the ICCD camera 23. In this case, although the measurement sensitivity is decreased because the array type semiconductor does not have an intensifying function by an image intensifier, production cost can be reduced because the array type semiconductor element is not expensive compared with the ICCD camera 23. The array type semiconductor element is suitable to the case of the strong emission intensity of the measuring substance.

A photomultiplier tube may be used instead of the ICCD camera 23. The following two methods are considered in the case of the use of the photomultiplier tube.

First, the general single-element photomultiplier tube may be used. Because the photomultiplier tube has the high sensitivity and large light reception area, the measurement sensitivity of the emission intensity is improved in the single wavelength. Measurement resolution can also be improved by narrowing a slit width of the spectrometer 22. However, in this case, because only the intensity of the single wavelength can be measured at once, it is necessary that an angle of a diffraction grating in the spectrometer 22 be changed to sequentially measure the intensity per each wavelength in order to obtain the emission spectrum necessary to identify the constituent of the measuring substance. In this case, because the laser beam intensity and concentration of the measuring substance are not always stabilized, the measuring conditions such as the laser beam intensity in each wavelength and the concentration of the measuring substance are possibly changed in changing the angle of diffraction grating. Therefore, there is a risk of measuring the incorrect emission spectrum. Particularly, in the case where the weak light is measured, it is necessary to integrate the light reception signal to improve the S/N ratio. When the light reception signal is integrated for a long time in each wavelength, it takes a long time to measure one emission spectrum. Therefore, preferably the method using the general single-element photomultiplier tube is applied in the case of the stable measuring conditions such as the laser beam intensity and the concentration of the measuring target substance.

Second, a multi-channel photomultiplier tube may be used. The multi-channel photomultiplier tube means photomultiplier tubes placed in array shape. The use of the multi-channel photomultiplier tube improves the measurement sensitivity of the emission intensity because the multi-channel photomultiplier tube has the high sensitivity and large light reception area per one element. Additionally, because the wide spectrum can be measured at once, the S/N ratio can be improved by the integration. However, usually the multi-channel photomultiplier tube has insufficient wavelength resolution because of the large area per one channel. Therefore, the particularly effective measurement is performed to the substance having the wide spectrum using the multi-channel photomultiplier tube.

Figure 6:
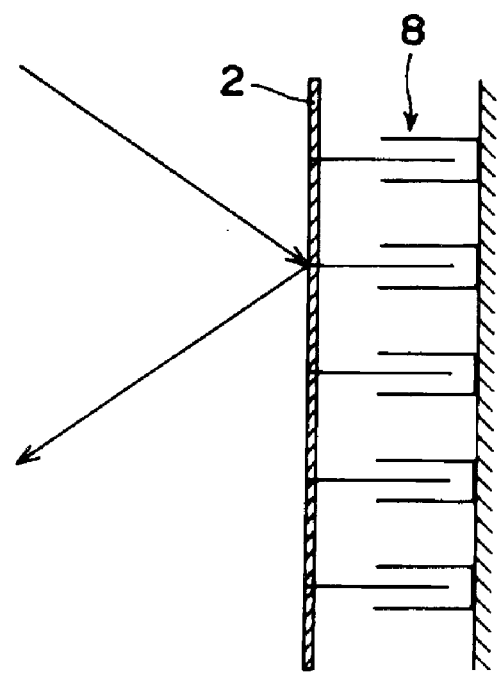
FIG. 6 is a principle view showing an example in which a filament forming method of the invention is implemented, FIG. 6 (A) shows an example in which the local projection and global recess are realized with one mirror, and FIG. 6 (B) shows an example in which the local projection and global recess are realized with a combination of two reflection mirrors.
Figure 6:
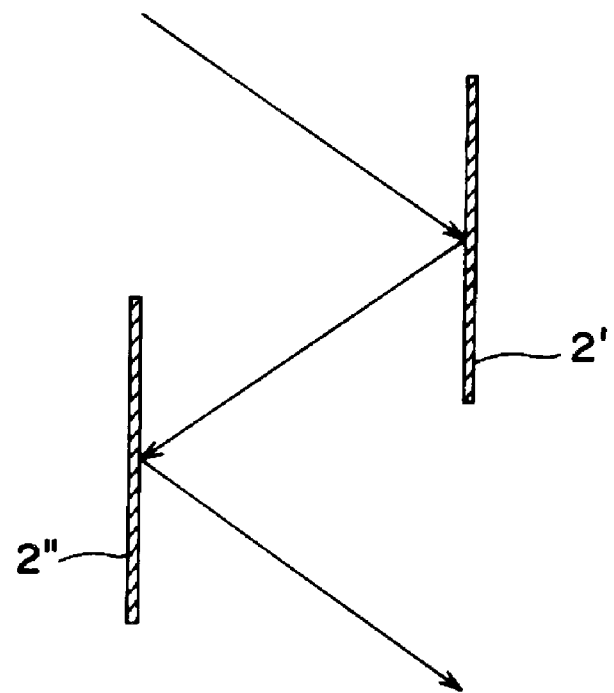

In the embodiments explained above, the local projection 9 or recess and the global recess 10 are formed using the deformable mirror 2 including one thin reflecting mirror as shown in FIG. 6(A) as the surface shape deformable mirror 18, and the process of generating the starting point for the filament generation and the process of gathering the energy of the ultrashort pulse laser beam or the surrounding intensity spots around the center intensity spot are simultaneously performed. Alternatively, as shown in FIG. 6(B), at least two mirrors of a first mirror 2' having the local projection 9 or recess and a second mirror 2" having the global recess 10 are combined on the optical path, and the two processes may be performed in tandem by the different reflecting mirrors. Therefore, the filament having arbitrary density can be generated at any position in the cross section of the reflected beam, or the filament generation position can arbitrarily be controlled by the control of the global recess forming position.

Figure 17:
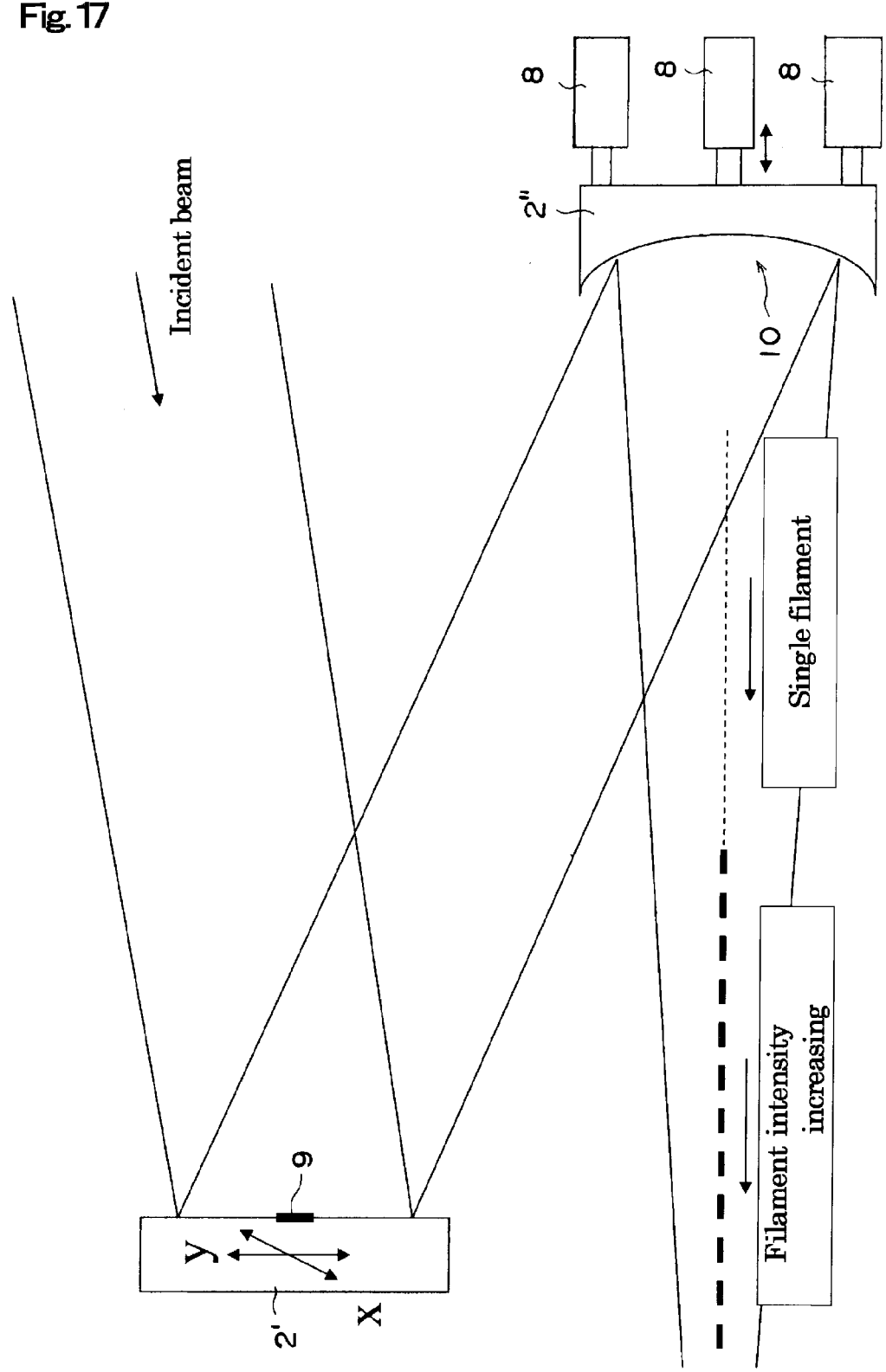
FIG. 17 is a principle diagram showing an example in which the local projection and global recess are realized with a combination of two mirrors.

In the case where the filament 14 is formed by the combination of the first mirror 2' having the local projection 9 or recess and the second mirror 2" in which the global recess 10 is formed, both the local projection 9 or recess of the first mirror 2' and the global recess 10 of the second mirror 2" may be formed in a fixed structure in which the local projection 9 or recess of and the global recess 10 are not displaced nor deformed, or both the local projection 9 or recess of and the global recess 10 may be formed in the movable structure. For example, as shown in FIG. 17, the first mirror 2' having the local projection 9 and a second mirror 2" including the deformable mirror which forms the global recess 10 at the position corresponding to surrounding of the local projection 9 in the beam cross section are disposed on the optical path of the ultrashort pulse laser beam, the intensity spot is formed at any position of the beam cross section while the ultrashort pulse laser beam 15 is reflected through the first and second mirrors 2' and 2", and the energy of the ultrashort pulse laser beam 15 or the surrounding intensity spots may be gathered around the intensity spot of itself or an arbitrary one or plural intensity spots in the plural formed intensity spots. Because the first reflecting mirror 2' and the second reflecting mirror 2" can separately be controlled, the position in the beam cross-section of the local projection 9 formed on the reflection plane can be changed by controlling the first reflecting mirror 2' in the x-y direction. The second reflecting mirror 2" including the deformable mirror includes the plural actuators 8 each of which can independently be controlled on the backside of the deformable mirror. Therefore, the reflection plane can be formed in the global recess 10 having any curvature by driving the actuators 8, or the formation position, intensity, and density of the filament can freely be controlled by the control of the curvature center position and shape of the global recess 10. In some cases, in the first reflecting mirror 2', another mirror in which the local projection 9 is formed at a different position is prepared, and the position of the local projection 9 or recess may be changed by the replacement of another mirror.

The above embodiments have the structure in which the rod 3 is directly bonded to the backside of the deformable mirror 2 with the bonding agent 7. Alternatively, the driving element of the actuator 8 or a front end portion of a member rigidly bonded to the driving element is directly bonded to the backside of the mirror, and the actuator 8 may directly support the deformable mirror 2.

In the above embodiments, the global recess 10 is provided to gather the energy of the ultrashort pulse laser beam 15 reflected around the filament 14 or the surrounding intensity spots around the intensity spot which becomes the starting point of the generation of the filament 14. Alternatively the global recess 10 may be omitted.

In the embodiments explained above, the filament 14 is generated by the irradiation of the ultrashort pulse laser beam 15, and the fine particles which is of the measuring target is irradiated with the filament 14 to generate the plasma. Alternatively, the plasma may be generated by focusing the ultrashort pulse laser beam 15 onto the fine particles.

The embodiments explained above relate to the measurement of the airborne fine particles. However, the invention is not limited to the airborne fine particles, but the invention can also be applied to the measurement of the fine particles in a living body, a liquid, and the like.

EXAMPLE 1

Figure 18:
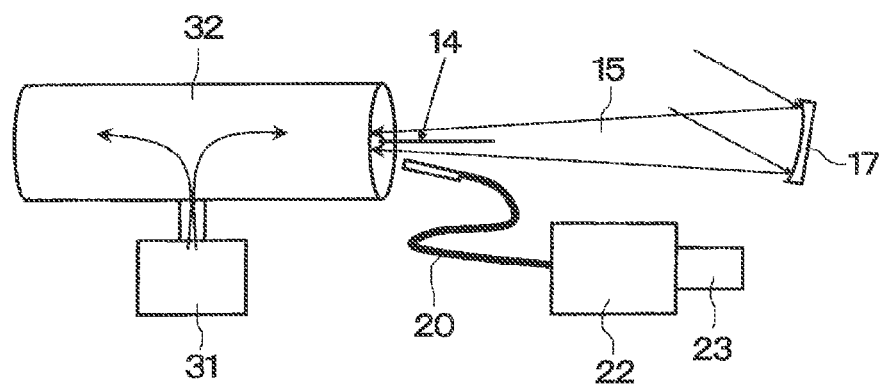
FIG. 18 is a schematic diagram showing an experimental system which measures in-situ sea-salt particles constituent.

Experiments were performed to confirm the effect of the invention. The in-situ measurement of Na in sea-salt particles was performed using the ultrashort pulse laser beam 15. FIG. 18 shows an experimental system. Saturated salt water (150 g/500 ml) was changed into the fine particles to generate synthetic sea-salt particles using an ultrasonic humidifier (fine particle generator) 31. When the sea-salt particles were measured using a particle diameter measuring device (not shown, VisiSizer product of Oxford lasers) in which a laser was used, the particle diameter of the aerosol (sea-salt particles) was not more than 10 μm. The generated sea-salt particles was sprayed in a cylinder 32 having an inner diameter of 20 cm and a length of 5 m. A chirped pulse amplification femtosecond titanium-sapphire laser device was used. The laser beam having the pulse energy of 130 mJ, pulse width of 70 fs, peak output of 2 TW, and pulse repetition of 10 Hz was focused using the concave mirror 17 having the focal distance of 20 m, and the sea-salt particles were irradiated with the laser beam. After the focusing, using the bundle fiber 20 placed backward at the angle of 23 degrees relative to the laser beam propagating direction, the emission of the sea-salt particles was introduced to the spectrometer 22 having the focal distance of 460 mm at the position of about 18 m. The spectrum was received by the ICCD camera 23.

Figure 19:
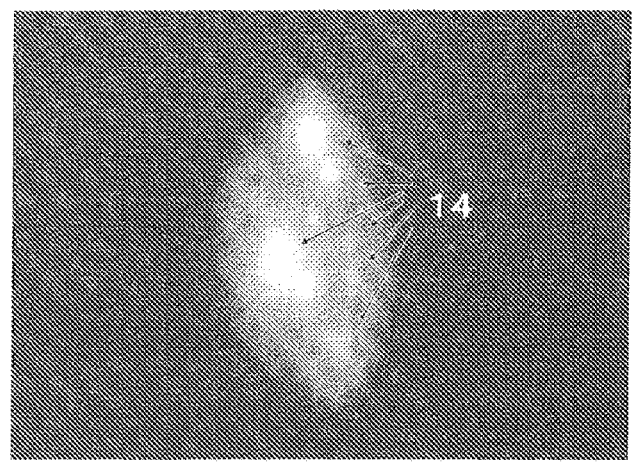
FIG. 19 is a view showing a cross section of a laser beam in which a filament is generated.
Figure 20:
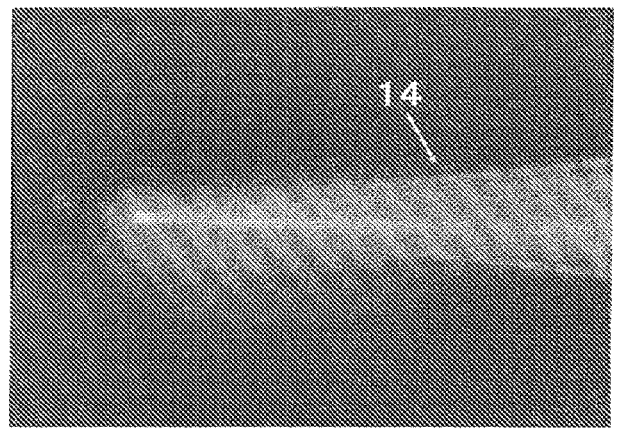
FIG. 20 is a reference view showing a state of multi-filament propagation.

FIG. 19 shows the laser beam cross section and the state of generated multifilament at sea-salt particles emission measurement point. Many bright spots observed in the laser beam are the filament 14. FIG. 20 is a reference drawing, and shows a multi-shot overlaid image of the laser beam incident to the cylinder filled with the water vapor from an obliquely crosswise direction. The propagation of each filament 14 is observed.

Figure 21:
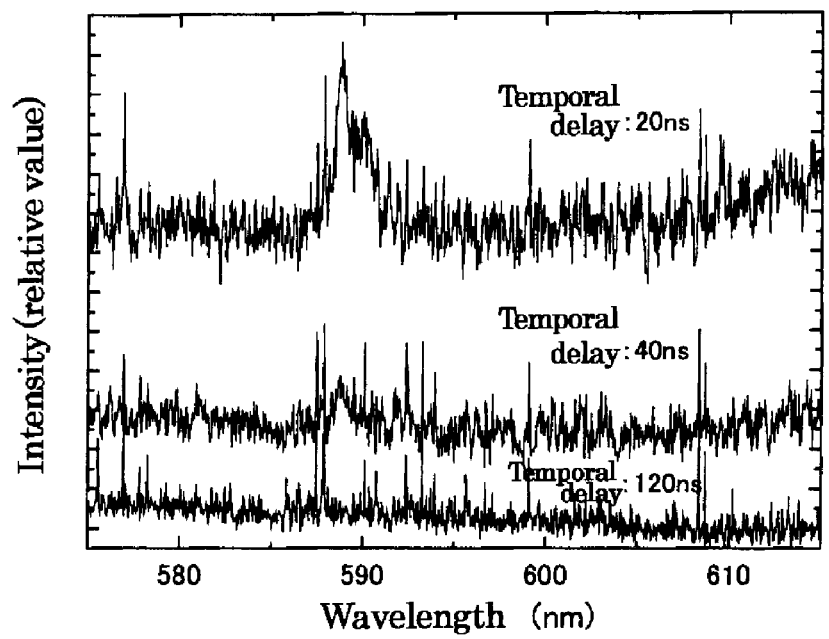
FIG. 21 shows a Na emission spectrum when sea-salt particles are irradiated with the filament, FIG. 21(*a*) is a view showing a change in an emission spectrum when a delay time is changed from a laser beam of gate timing of an ICCD camera, and FIG. 21(*b*) is a drawing showing an emission spectrum of an alcohol lamp in which salt is dissolved.
Figure 21:
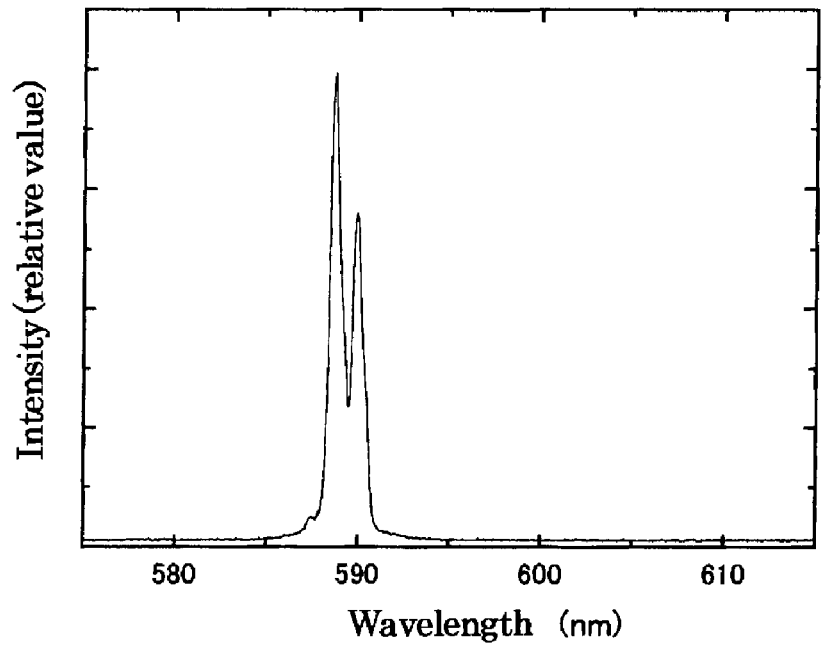

FIG. 21($a$) shows the result of the spectral measurement when the sea-salt particles is irradiated with the filament 14. The gate width of the ICCD camera 23 was set to 20 ns in the measurement. There is a jitter of about 10 ns in the irradiation timing of the ultrashort pulse laser beam 15. The gate timing of the ICCD camera 23, when the strongest white light generated by a basic wave and self-phase modulation of the titanium-sapphire laser was observed, was found by setting the center wavelength of the spectrometer 22 to 800 nm. FIG. 21(*a*) shows spectra of the delay times of 20 ns, 40 ns, and 120 ns from the found gate timing. FIG. 21(*b*) shows an emission spectrum of an alcohol lamp, in which salt is dissolved, as the reference spectrum. In FIG. 21(*b*), $D_1$ and $D_2$ lines of Na are clearly observed.

In FIG. 21(*a*), Na emission was clearly observed at the delay time of 20 ns (when temporal delay of 20 ns was given), in the case where the sea-salt particles were irradiated with the filament 14. In the case of the delay time of 40 ns (temporal delay of 40 ns), the Na emission was hardly observed. In the case of the delay time of 120 ns (temporal delay of 120 ns), no Na emission was observed. In the case of the delay time of 20 ns, the reason why the signal intensity is gradually raised on the longer wavelength side is that the white light is generated. The white light intensity is weakened as the delay time is lengthened. In the case of the delay time of zero, i.e., in the case where the gate timing of the ICCD camera 23 is substantially identical to the laser irradiation, the Na emission was not observed while hidden behind the spectrum of the white light. The above results shows that the gate timing of the ICCD camera 23 is adjusted to measure the emission spectrum of the plasma generated in the filament 14 and whereby the sea-salt particles can be identified.

EXAMPLE 2

Figure 22:
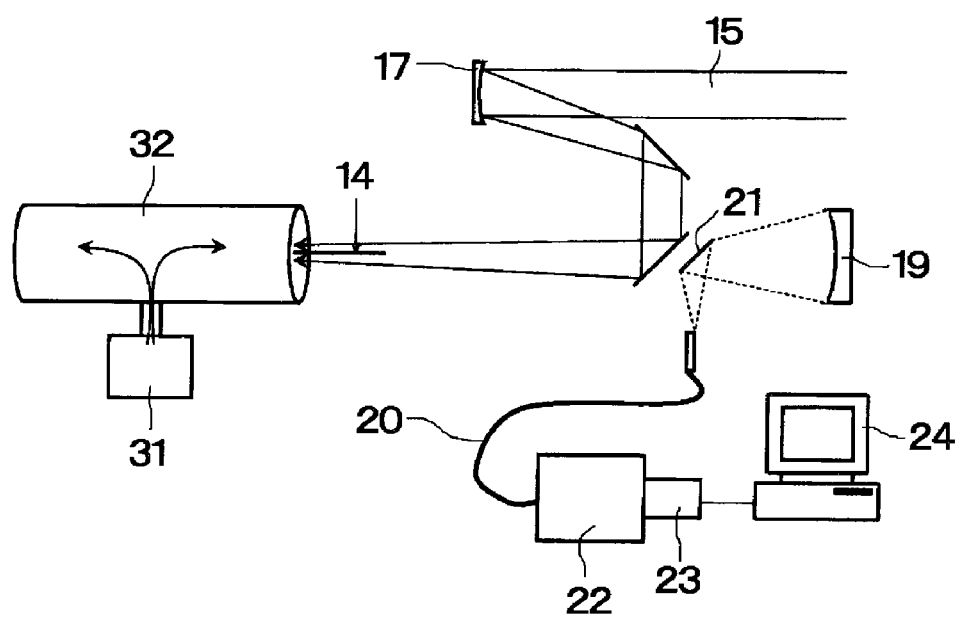
FIG. 22 is a schematic diagram showing an experimental system which remotely measures sea-salt particles constituent.

A lidar measurement experiment of the sea-salt particles was performed based on the above result. FIG. 22 shows an experimental system of the lidar measurement experiment. Similarly to the in-situ measurement, the filament 14 was generated by focusing the ultrashort pulse laser beam 15 using the concave mirror 17 having the focal distance of about 20 m, and the synthetically-generated sea-salt particles was irradiated with the filament 14. A Newtonian receiver telescope having a primary mirror diameter of 12.5 inches and focal distance of 1.5 m was used as the receiver telescope 19. The receiver telescope 19 was placed about 20 m short of the sea-salt particles while being coaxial with the ultrashort pulse laser beam 15. The light focused by the receiver telescope 19 was incident to the spectrometer 22 through the bundle fiber 20. The light outgoing from the bundle fiber 20 was incident to the spectrometer 22 having the focal distance of 460 mm, and the spectrum was received by the ICCD camera 23.

Figure 23:
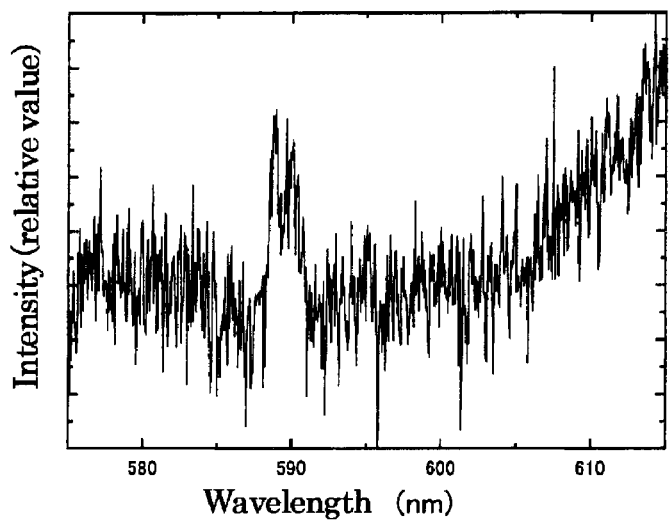
FIG. 23 shows remote measurement result with the filament for a Na emission spectrum in the sea-salt particles, FIG. 23(*a*) is a drawing showing the Na emission spectrum in the sea-salt particles.
Figure 23:
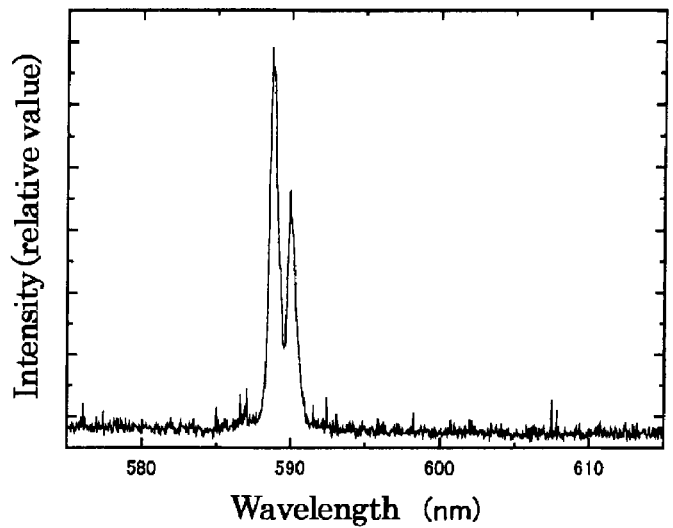

FIG. 23 shows the measured result. The reference spectrum shown in FIG. 23(*b*) is the emission spectrum of the alcohol lamp in which the salt is dissolved, and the $D_1$ and $D_2$ lines of Na are clearly observed in FIG. 23(*b*). The spectrum shown in FIG. 23(*a*) is one which obtained by the remote measurement in which the sea-salt particles is irradiated with a T-cube laser beam. Background data which is measured without irradiating the sea-salt particles with the laser beam is subtracted in the spectrum shown in FIG. 23(*a*). At this point, similarly to the in-situ measurement, the gate delay time of the ICCD camera 23 was set to 20 ns relative to the laser beam. As can be seen from the spectral shape, the $D_1$ and $D_2$ lines of Na are observed in the sea-salt particles. Accordingly, it was confirmed that the lidar measurement of the fine particles having the particle diameters of 10 µm or less could be performed by the invention.

The invention claimed is:

1. A fine-particle constituent measuring method characterized in that an ultrashort pulse laser beam is focused to fine particles to generate plasma and a constituent of said fine particles is measured based on an emission spectrum from the plasma, the ultrashort pulse laser beam including a filament generated by irradiation thereof, a reflecting mirror having a local projection or recess being irradiated with the ultrashort pulse laser beam, and an intensity spot being formed at any position of a beam cross-section reflected from the local projection or recess and set to a starting point of the filament generation.

2. The fine-particle constituent measuring method according to claim 1, wherein a recess which is global relative to the local projection or recess is provided around the local projection or recess of the reflecting mirror, and
   energy of the ultrashort pulse laser beam reflected by the global recess or the surrounding intensity spots are gathered around the intensity spot which becomes the starting point of the filament generation.

3. The fine-particle constituent measuring method according to claim 1, wherein the reflecting mirror is a deformable mirror whose reflection plane can arbitrarily be deformed.

4. The fine-particle constituent measuring method according to claim 1, wherein white-light spectral intensity is reduced by giving a temporal delay to measurement of the emission spectrum.

5. The fine-particle constituent measuring method according to claim 1, wherein light emitted from the plasma is focused using a receiver telescope.

6. A fine-particle constituent measuring method characterized in that an ultrashort pulse laser beam is focused to fine particles to generate plasma and a constituent of said fine particles is measured based on an emission spectrum from the plasma, the ultrashort pulse laser beam including a filament generated by irradiation thereof, a reflecting mirror having a local projection or recess being irradiated with the ultrashort pulse laser beam, and an intensity spot being formed at any position of a beam cross-section reflected from the local projection or recess and set to a starting point of the filament generation,
   a reflecting mirror having a global recess also being irradiated with the ultrashort pulse laser beam, the global recess being global relative to the local projection or recess, the global recess being provided around the local projection or recess of the beam cross-section, and
   energy of the ultrashort pulse laser beam reflected by the global recess or the surrounding intensity spots being gathered around the intensity spot which becomes the starting point of the filament generation.

7. The fine-particle constituent measuring method according to claim 6, wherein white-light spectral intensity is reduced by giving a temporal delay to measurement of the emission spectrum.

8. The fine-particle constituent measuring method according to claim 6, wherein light emitted from the plasma is focused using a receiver telescope.

9. A fine-particle constituent measuring apparatus comprising:
   a laser device which outputs an ultrashort pulse laser beam;
   a beam-focusing device which focuses the ultrashort pulse laser beam to irradiate fine particles;
   a light reception device which receives plasma generated from the fine particles by the focusing of the ultrashort pulse laser beam; and a spectrum analyzer which identifies a constituent of the fine particles based on an emission spectrum from the plasma;

the beam-focusing device forming an intensity spot in the ultrashort pulse laser beam to generate a filament during a process of focusing the ultrashort pulse laser beam, the beam-focusing device including a reflecting mirror having a local projection or recess, and the reflecting mirror being irradiated with the ultrashort pulse laser beam, and an intensity spot being formed at any position of a beam cross-section reflected from the local projection or recess and set to a starting point of the filament generation.

10. The fine-particle constituent measuring apparatus according to claim 9, wherein a recess which is global relative to the local projection or recess is provided around the local projection or recess of the reflecting mirror of the beam-focusing device, and energy of the ultrashort pulse laser beam reflected by the global recess or the surrounding intensity spots are gathered around the intensity spot which becomes the starting point of the filament generation.

11. The fine-particle constituent measuring apparatus according to claim 9, wherein the beam-focusing device includes a first reflecting mirror and a second reflecting mirror which are disposed on a path for focusing the ultrashort pulse laser beam, the first reflecting mirror and second reflecting mirror continuously reflecting the ultrashort pulse laser beam, the first reflecting mirror has the local projection or recess in a reflection plane thereof, the second reflecting mirror has a reflection plane which forms a global recess at a position corresponding to a surrounding of the local projection or recess of the beam cross-section, the global recess being global relative to the local projection or recess of the first reflecting mirror, and the beam-focusing device forms an intensity spot in an arbitrary position of a cross section of the beam reflected by the first reflecting mirror, and the beam-focusing device gathers energy of the ultrashort pulse laser beam reflected by the second reflecting mirror or the surrounding intensity spots around the intensity spot which becomes the starting point of the filament generation.

12. The fine-particle constituent measuring apparatus according to claim 9, wherein the reflecting mirror is a deformable mirror whose reflection plane can arbitrarily be deformed.

13. The fine-particle constituent measuring apparatus according to claim 9, wherein the light reception device reduces white-light spectral intensity by giving a temporal delay to measurement of the emission spectrum.

14. The fine-particle constituent measuring apparatus according to claim 9, wherein the light reception device includes a receiver telescope which focuses light emitted from the plasma of the fine particles.

* * * * *